United States Patent
Hayashi et al.

(10) Patent No.: US 6,593,096 B1
(45) Date of Patent: Jul. 15, 2003

(54) IMMUNOTHERAPEUTIC AGENT FOR CANCER CONTAINING NUCLEOIDAL COMPONENT OF BACTERIUM AS ACTIVE INGREDIENT

(76) Inventors: Akira Hayashi, 9-5, Tsukumodia 3-chome, Suita-shi, Osaka (JP); Ichiro Azuma, 3-2, Makomanaikami-machi 5-chome, Minami-ku, Sapporo-shi, Hokkaido (JP); Kumao Toyoshima, 13-3-1404, Nakano-cho 5-chome, Miyakojima-ku, Osaka-shi, Osaka (JP)

( * ) Notice: Subject to any disclaimer, the term of this patent is extended or adjusted under 35 U.S.C. 154(b) by 0 days.

(21) Appl. No.: 09/380,566
(22) PCT Filed: May 28, 1997
(86) PCT No.: PCT/JP97/01805
§ 371 (c)(1), (2), (4) Date: Dec. 20, 1999
(87) PCT Pub. No.: WO98/39017
PCT Pub. Date: Sep. 11, 1998

(30) Foreign Application Priority Data

Mar. 7, 1997 (JP) .................................. 9-53472

(51) Int. Cl.$^7$ ................... G01N 33/554; G01N 33/569; A61K 39/385; A61K 39/00; A61K 35/14
(52) U.S. Cl. .................... 435/7.32; 424/197.11; 424/198.1; 514/800; 530/385
(58) Field of Search .................. 530/385; 435/7.32; 514/800; 424/197.1, 198.1

(56) References Cited

FOREIGN PATENT DOCUMENTS

| JP | 56-32491 A | 4/1981 |
| JP | 59-161320 A | 9/1984 |
| JP | 9-3091 A | 2/1997 |

OTHER PUBLICATIONS

Janeway, Jr. et al, Immunobiology, 1997, Garland Publishing, Inc., Third Ed., pp. 11:20–11:21.*
Hayashi et al, Proc. Japan Acad, 1994, vol. 70, pp. 205–209, entire document.*
Takeshi Ogura et al.; Gann, 69, pp. 311–315; Jun. 1978; XP–000974087.
Akira Hayashi, Proc. Japan Acad. vol. 70, Ser. B, (1994), p. 205–209.

* cited by examiner

Primary Examiner—Anthony C. Caputa
Assistant Examiner—Natalie Davis
(74) Attorney, Agent, or Firm—Birch, Stewart, Kolasch & Birch, LLP (57) ABSTRACT

An agent for cancer immunotherapy with independent use, containing bacterial components as an active ingredient, which induces cancer patients to exhibit immune responsiveness, as indicated by the increase of interferon-γ and CD28 markers in peripheral blood, when administered to an immuno-competent patient intracutaneously.

9 Claims, 10 Drawing Sheets

(2 of 10 Drawing Sheet(s) Filed in Color)

↓ :100γ of BCG-CWS was inoculated intradermally, and each biological index was determined before and, 18 hr, 42hr, 7 d, 15 d, 21 d and 28 days after inoculation A: cytokine level in peripheral blood; G-CSF(○), IL-12(●) and IFN-γ(✗)
B: blood cell count in peripheral blood; WBC(○), RBC(●) and PLT(✗)
C: white cell count in peripheral blood; granulocyte(○), lymphocyte(●) and monocyte(✗)

| | | | | |
|---|---|---|---|---|
| Lung cancer: 75 | (Stage I:14, | II: 9, | III:26, | IV:26) |
| Stomach cancer: 21 | (Stage I: 1, | II: 4, | III: 4, | IV:12) |
| Colon cancer: 16 | (Stage I: 1, | II: 5, | III: 0, | IV:10) |
| Breast cancer: 7 | (Stage I: 1, | II: 0, | III: 2, | IV: 4) |
| Pharyngeal cancer: 7 | (Stage I: 0, | II: 0, | III: 0, | IV: 7) |
| Cancers in oral cavity: 5 | (Stage I: 0, | II: 0, | III: 1, | IV: 4) |

Acute myelocytic leukemia : 5

RAEB (Refractory anemia with excess of blast): 4
Pancreatic cancer : 4
Ovarian cancer: 4

Others: Malignant thymoma 3, Hepatoma 3, Uterine Portio cancer 3, Leiomyosarcoma 2, Maxillary cancer 2, Prostate cancer 2, Retinoblastoma 2, Esophageal cancer 2, Gall duct cancer 2, Vaginal cancer 2, Uterine corpus cancer 2, Malignant lymphoma 2, Thyroid cancer 1, Bladder cancer 1, Chorionepithelioma malignum 1, Renal cell cancer 1, Malignant mesothelioma 1, Malignant mesenterioma 1

Total 181 cases (1974-1996)

| surgical operation | The number of cases | stage (The number of cases) | Alive (%) | Dead (%) | IFN-γ induction (%) |
|---|---|---|---|---|---|
| + | 36 | I(12) | 12(100) | 0( 0) | 11 ( 92) |
|   |    | II( 5) | 5(100) | 0( 0) | 5 (100) |
|   |    | III(14) | 14(100) | 0( 0) | 13 ( 93) |
|   |    | IV( 5) | 1( 20) | 4( 80) | 3 ( 60) |
| - | 23 | I( 0) |  |  |  |
|   |    | II( 1) | 1(100) | 0( 0) | 1 (100) |
|   |    | III( 6) | 4( 67) | 2( 33) | 3 ( 50) |
|   |    | IV(16) | 2( 13) | 14( 87) | 4 ( 25) |

▼ : 100γ of BCG - CWS was inoculated intradermally, and each biological index was determined before and, 18hr, 42hr, 1wk, 2wk, 3wk 4wk 5wk and 6wk after inoculation A : Change in averaged fluorescence intensity of a marker on the surface of lymphocytes; CD28(○) and CD46(●)

B : cytokine level in peripheral blood; IFN - γ (○), G - CSF(●) and IL - 12(×)

C : white cell count in peripheral blood; granulocyte(○), lymphocyte(●) and monocyte(×)

Fig. 10

IMMUNOTHERAPEUTIC AGENT FOR CANCER CONTAINING NUCLEOIDAL COMPONENT OF BACTERIUM AS ACTIVE INGREDIENT

This application is the national phase under 35 U.S.C. §371 of PCT International Application No. PCT/JP97/01805 which has an International filing date of May 28, 1997, which designated the United States of America.

DETAILED DESCRIPTION OF THE INVENTION

1. Field of the Invention

The present invention relates to an agent for cancer immunotherapy containing bacterial components as an active ingredient, and more particularly, a new agent used independently for cancer patients having immuno-competence. More specifically, the invention relates to a new immunotherapeutic agent capable of preventing recurrence of cancer or generation of secondary cancer including post-operative metastasis, in patients having immuno-competence which can be determined by an ability of inducing interferon-$\gamma$ (IFN-$\gamma$) and the like. The invention further relates to a new method for determining immuno-competence of a patient by measuring an ability of inducing IFN-$\gamma$ and so on, which is used for the present cancer immunotherapy.

2. Prior Art

An agent for cancer immunotherapy containing bacterial components as an active ingredient is known, and particularly, numerous clinical data obtained by the cancer immunotherapy using BCG (Bacille Calmette-Guerin) have been accumulated.

There have been widely reported the results of clinical trials on cancer immunotherapy, in particular, since clinical effects of BCG-immunotherapeutic agents were confirmed by Mathe et al. in acute lymphocytic leukemia and by Molton et al. in melanoma in the latter half of 1960's. However, since the clinical data have been stochastically analyzed for the survival rates in the randomized controlled trial, ineffective cases have increased in immunotherapy with BCG, resulting in the doubt of its effectiveness. After that, BCG was used only supplementarily in chemotherapy. In addition to BCG, bacteria such as *C. parvum*, hemolytic Streptococcus, and OK432 have also been used. However, in cancer immunotherapy with those bacteria, some were effective and some were ineffective like BCG, and their effectiveness has not been established yet.

Recently, in BCG-immunotherapy, cell wall skeleton (CWS) prepared from cell walls, obtained by grinding bacterial cells and then fractionating by centrifugation, has been used to make improvements in terms of prevention of side effects and regulation of dose and frequency of administration. Clinical trials for lung cancer, leukemia, stomach cancer and the like using BCG-CWS or N. rubra-CWS were conducted under randomized design by Yamamura et al. of Osaka University and their associates. Though the results showed the stochastically significant prolongation of survival time, it was incomplete as a cancer immunotherapy. At present, an established reputation for such immunotherapeutic agents can be seen in Iwanamikoza, Immunoscience 7, Transplantation Immunity and Tumor Immunity, Feb. 29, 1984, p.302, which reads "The results, as already stated have failed to show constant effectiveness as an immunotherapeutic agent, because we obtained adverse, ineffective, or insignificant effect. The major reason, among others, for such inconsistency is attributed to the fact that the statistical significance test was performed between the group in which immunotherapy was used as a supplemental therapy and the group in which immunotherapy was not used as a supplemental therapy. Thus, these results suggest the limit of the immunotherapy which does not exert direct anti-cancer effects."

The inventors had doubts about the ways in which the cancer immunotherapy using BCG-CWS has been done in the past, analyzed the problems contained in this immunotherapy, and noticed the fact that such immunotherapy had been conducted together with a therapy which has a strong immuno-suppressive effect, such as anti-cancer drug and radiation. The inventors thought that a combination of immunostimulation therapy using BCG-CWS, N.rubra-CWS and so on, and a chemotherapy having immuno-suppressive effect would offset the characteristics of each therapies, and therefore, the combination contains discrepancy. Then, the inventors considered that, in order to show the effectiveness of the cancer immunotherapy with BCG-CWS, N.rubra-CWS or the like, an establishment of administration method which can easily induce immunostimulation, and selection of patients having suitable immuno-competence would be important.

The inventors have discovered that a therapy with independent use of BCG-CWS alone after the initial treatment has shown excellent therapeutic effects not found in the combination of the therapy with BCG-CWS and chemotherapy (Pro. Japan Acad.,70,Ser.B 205–209(1994)). It was also found that, based on the analysis of peripheral blood from treated patients, patients who showed evident induction of IFN-$\gamma$ by intradermal administration of BCG-CWS survived in good health, including complete cure, and on the other hand, patients who did not show the induction of IFN-$\gamma$ died in a short time. The inventors have additionally found that the induction of IFN-$\gamma$ by inoculation of BCG-CWS directly correlates to anticancer effects (Japanese Cancer Association, 54th Meeting, No.2411, 1995).

According to the above findings, the inventors made extended study in order to establish a cancer immunotherapy using bacterial components alone as an active ingredient. As a result, it was found that CD28 as well as IFN-$\gamma$ and G-CSF are useful as a marker of immuno-competence after inoculation of bacterial components in order to recognize a patient who has immuno-competence suitable for the present therapy. The inventors also discovered that an initial therapy has a great influence on the maintenance of an appropriate immuno-competence of a patient, and selection of such initial therapy is of great importance.

The present invention is based on the above findings.

The cancer immunotherapy which has been established by the present invention is summarized as follows.

The immunotherapy with BCG-CWS and the like is effective, as a matter of course, only in patients who have immuno-competence. Since the immuno-competence is affected by initial therapy to be used, it is essential that the therapy with independent use of BCG-CWS alone should be performed after removing as much cancer cells as possible by, for example, surgical operation, and discontinuing a chemotherapy or radiation which possibly decreases immuno-competence of patients.

Upon inoculation of BCG-CWS, a series of transient alterations are observed in components of peripheral blood from a patient. The alterations closely relate to the effectiveness of the immunotherapy as follows:

(1) Alterations in components of peripheral blood from a patient to whom the immunotherapy was effective.

As for cellular components, increase in leukocytes, particularly increase in granulocytes, and decrease in lymphocytes (continue about 24 hours) are found, with the increase and decrease having their peaks at from about 15 hours to about 18 hours after inoculation.

As for cytokines, increase in IFN-γ (continues about 30 hours) and G-CSF (continues about 1 week) is found.

As for markers on the surface of T cell, increase in high CD28-positive lymphocytes (continues about 4–6 weeks) is found.

(2) Alterations in components of peripheral blood from patients to whom immunotherapy was not effective.

No alteration of cellular components, cytokines, or markers on the surface of T-cell was found.

In three patients to whom immunothrapy was effective, increase of CD28-positive lymphocytes was not found. At the beginning of the therapy, those patients continued to show recovery. However, metastasis to the brain was found around after 2 years in two patients and they eventually died.

Accordingly, we considered that IFN-γ and CD28 are useful as markers to know immuno-competence which gives anticipation on the results of the therapy. Influence of pre-treatment including initial therapy on the immuno-competence was investigated, especially in terms of inducibility of IFN-γ, to give the following findings.

(1) In about 90% of the patients who did not receive any pre-treatment, such as chemotherapy and radiation therapy, which may influence to immuno-competence, induction of IFN-γ was observed owing to a therapy with independent use of BCG-CWS alone.

(2) In only about 30% of the patients who received pre-treatment, such as chemotherapy and radiation therapy, which influences to immuno-competence, induction of IFN-γ was observed owing to a therapy with independent use of BCG-CWS alone.

(3) Great difference that was observed in the survival rates is as follows: About 90% of the patients who were positive in IFN-γ induction survived more than 6 months after the beginning of the treatment with BCG-CWS. On the other hand, only about 20% of the negative patients who failed to induce IFN-γ, survived more than 6 months after the beginning of the treatment with BCG-CWS.

Accordingly, it has been demonstrated that a therapy with independent use of BCG-CWS alone is desirable as a cancer immunotherapy after removing as much cancer cells as possible by surgical operation, and discontinuing therapy with chemotherapy and radiation which are considered to decrease immuno-competence.

On the basis of the above findings, the present invention has been completed, which is summarized as follows:

(1) An agent for cancer immunotherapy with independent use, which contains bacterial components as an active ingredient, said components inducing immuno-competence in a cancer patient when administered intracutaneously, said immuno-competence being detectable by increases of IFN-γ and a population of high CD28-positive lymphocytes in blood-level.

(2) An agent for cancer immunotherapy as stated in Item (1), characterized by that said agent is to be administered to the following patients and suppresses recurrence of the cancer or occurrence of secondary cancer:

(a) a patient who is not suffering from lowering of immuno-competence, and (b) a patient who does not have distant metastasis including that in the brain, liver, or bone.

(3) An agent for cancer immunotherapy as stated in Item (2), characterized by that said agent is to be administered to a cancer patient who has had remission induction or operation for removing primary lesion on initial therapy.

(4) An agent for cancer immunotherapy as stated in Item (3), wherein the patient is the one having solid cancer, and the initial therapy is a surgical operation.

(5) An agent for cancer immunotherapy as stated in Item (3), wherein the patient is the one having non-solid cancer, and the initial therapy is chemotherapy.

(6) An agent for cancer immunotherapy as stated in Item (1), characterized by treating metastasis of cancer to the lymph node.

(7) An agent for cancer immunotherapy as stated in Item (1), wherein the patient is the one suffering from lung cancer.

(8) A method of testing immuno-competence in an immunotherapy with independent use, comprising determining the level of IFN-γ and CD28 marker in blood obtained from a cancer patient who were administered bacterial components intracutaneously.

The first embodiment of the invention is an agent for cancer immunotherapy with independent use containing bacterial components as an effective ingredient. As the bacterial components, a known adjuvant for anti-cancer immunity is applicable (see Iwanamikoza, Immuno Science 7,p.265, Table 5.2, 1984). For example, BCG-CWS, N.rubra-CWS, and the like are preferable, and BCG-CWS is more preferable.

An agent for cancer immunotherapy with independent use according to the present invention is preferably administered to a patient, in which the agent induces immuno-competence when administered intracutaneously, said immuno-competence being detectable by increases in blood level of IFN-γ and CD28 markers in the patient.

An agent for cancer immunotherapy with independent use according to the present invention is a non-specific immunotherapeutic agent, and therefore, may be applied to any sorts of cancers, for example, lung cancer, stomach cancer, colon cancer, breast cancer, lingual cancer, laryngeal cancer, acute myelocytic leukemia, pancreatic carcinoma, ovarian cancer, and the like.

Up to now, the agent for cancer immunotherapy with independent use according to the present invention was administered to 181 cancer patients, and among them the number of the patients suffering from lung cancer was the largest (75 patients). The patients tested covered almost all sorts of cancers, including stomach cancer, colon cancer, breast cancer, etc.

The second embodiment of the invention shows that the following patients are preferable as a subject to which the agent for cancer immunotherapy according to the invention is applied:

(a) a patient who is not suffering from lowering of immuno-competence, and (b) a patient who does not have distant metastasis including that in the brain, liver, bone, or the like.

In addition, the agent for cancer immunotherapy according to the invention can be used as a continued maintenance therapy to suppress recurrence of the cancer including metastasis or occurrence of secondary cancer.

In the third embodiment of the invention, the agent for cancer immunotherapy according to the invention is preferably administered to a patient suffering from acute myelocytic leukemia who has had remission induction, or a patient suffering from a cancer who has received operation for removing primary lesion during initial therapy.

In the fourth embodiment of the invention, an agent for cancer immunotherapy of the invention is preferably administered alone to a patient having a solid cancer who received operation for removing primary lesion as much as possible. The solid cancer includes lung cancer, stomach cancer, colon cancer, and so on. Lung cancer is preferable.

In the fifth embodiment of the invention, an agent for cancer immunotherapy of the invention is preferably administered to a patient having a non-solid cancer who had remission induction by chemotherapy in initial therapy. The non-solid cancer includes leukemia and the like, and preferably, acute myelocytic leukemia.

In the sixth embodiment of the invention, an agent for cancer immunotherapy of the invention suppresses metastasis of cancer from primary lesion, and it is effective particularly to a cancer which has metastasized in the lymph node. The agent is significantly effective to an immunocompetent patient who showed IFN-γ induction, and the treatment with the agent resulted in disappearance of a fairly large metastasis in the lymph node. It was demonstrated that the agent is poorly effective to a patient who has had metastasis of cancer in the liver, brain, bone, and the like, before the beginning of the immunotherapy, even if the agent could induce IFN-γ in the patient. The reason why the agent for cancer immunotherapy of the invention, particularly, the immunotherapeutic agent comprising BCG-CWS, is effective to metastasis of cancer in the lymph node would be that an activation of a cytotoxic T lymphocyte (CTL) which acts specific to particular cancers is directly related to CD28 marker. That is, an increase in CD28 marker means an increase in a population of high CD28-positive lymphocytes, i.e., an activation of cancer-specific CTL.

In the seventh embodiment of the invention, an agent for cancer immunotherapy of the invention is used for a patient suffering from lung cancer. As will be stated below, therapeutic effects of the agent of the invention were analyzed in detail about a group of patients suffering from lung cancer, which is the largest group among the cases we have handled.

The eighth embodiment of the invention is a method of testing peripheral blood in order to select a patient suitable for the administration of the agent for cancer immunotherapy of the invention. Specifically, in a method of determining whether or not a patient has an ability of IFN-γ induction, blood samples are obtained, before and 18 hours after inoculation of 100γ or 200γ of BCG-CWS, and IFN-γ level in peripheral blood is measured to determine whether IFN-γ induction is positive or not. Suitable time when the above determination is performed may be when the fourth sensitization is conducted, during which BCG-CWS induces immune response, and when the first treatment is conducted, which permits earlier determination as to whether the immunotherapy should be continued or not. A population of high CD28-positive lymphocytes in peripheral blood may be determined according to any known method, for example, flow cytometry.

In addition, according to this embodiment, there are provided not only a method of detecting a cancer patient to whom the independent immunotherapy is applicable as a continued maintenance therapy for cancer that follows an initial therapy, but also a method of detecting a patient to whom the immunotherapy is not suitable and other therapies should be applied. According to this embodiment of the invention, surgical operation followed by an immunotherapy with independent use of BCG-CWS alone can be applied to a patient who can induce IFN-γ, and other therapy can be applied at early stage to a patient who cannot induce IFN-γ. Thus, an appropriate therapeutic program following initial therapy can be established depending on immunocompetence of a patient.

Preparation of BCG-CWS Inoculant

BCG-CWS may be prepared according to the method described in Azuma et al., J. Natl.Cancer Inst. 52:95–101 (1974).

BCG-CWS inoculant may be prepared according to the method described in Hayashi, A, Proc. Japan Acad.,70, Ser.B (1994)

Namely, BCG-CWS powder is placed in a 5 mL grinder tube, mineral oil (Drakeol-6VR; Pennsylvania Refining Co., Butler, U.S.A.) is added into the tube at the ratio of one drop per mg of BCG-CWS using 26G of injection needle, and then, the mixture was ground to smooth paste. 1.1% Tween 80 solution in saline is added to the mixture, which is then homogenized. The final concentration of a uniform suspension of small oil droplets containing BCG-CWS is 1 mg/mL. The oil attached BCG-CWS suspension was sterilized by incubating at 60° C. for 30 minutes.

Inoculation Schedule

Throughout the present study, BCG-CWS is always inoculated alone.

The inoculation schedule is divided into sensitization phase and therapeutic phase. In the sensitization phase, usually 200γ of BCG-CWS is intracutaneously inoculated once a week, totally four times, at the right and left lateral brachiums alternately. In the therapeutic phase, interval of the inoculations is extended to every four weeks. The amount of BCG-CWS to be inoculated is selected from between 10 and 250γ, preferably between 25 and 200γ, depending on biological responses of a patient.

Biological Response as an Index for Determining the Amount of BCG-CWS to be Administered Biological responses as an index for determining the amount of BCG-CWS to be administered are classified to local biological responses and systemic biological responses.

(1) Local Biological Responses

Primary local biological responses include skin reactions at the spot of injection. Specifically, they are flare, induration, and formation of ulcer. Swelling of the local lymph node, i.e., lymphangitis and lymphadenitis extending from the injection spot to the attending lymph node may occur occasionally, but it is always transient.

(2) Systemic Biological Response

The following transient over-response may occur due to interaction between the sensitivity of a patient and the amount of BCG-CWS inoculated, although it can be reduced by decreasing the amount of BCG-CWS to be inoculated.

Clinical symptoms: general malaise, fever, anorexia, and sometimes, nausea and vomiting.

Clinical test: leukocytosis, increased C reactive protein (CRP), and sometimes, slightly increased GOT and GPT.

In the case of a patient who does not show the local and systemic biological responses mentioned above, therapeutic effects of immunotherapy with BCG-CWS can not be expected.

Determination of Inductivity of IFN-γ

Effects of immunotherapy with BCG-CWS can be predicted by determining inductivity of IFN-γ.

Such determination is performed at the fourth inoculation in the sensitization phase (S4) and at the first inoculation in the therapeutic phase (T1). Peripheral blood is obtained before, and 18 hours after inoculation of BCG-CWS, and the blood level of IFN-γ is determined. When the level of IFN-γ increases more than 35 pg/mL by inoculation of BCG-CWS, induction of IFN-γ is judged as positive.

Determination of Induction of CD28-positive T-cells

Effects of immunotherapy with BCG-CWS can be predicted by determining induction of CD28 in the similar manner stated above.

Peripheral blood is obtained before, and 18 hours after inoculation of BCG-CWS, and increase in a population of high CD28-positive lymphocytes in the blood is determined.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 2A shows the level of cytokines (G-CSF, IL-12, IFN-$\gamma$) in peripheral blood, FIG. 2B shows the number of blood cells (white blood cell, red blood cell, platelet), and FIG. 2C shows the number of white blood cell (granulocyte, lymphocyte, monocyte) in peripheral blood.

FIG. 9A shows the level of markers expressed on the surface of lymphocytes (CD28 and CD46), and FIG. 9C shows the number of leukocytes (granulocyte, lymphocyte and monocyte) in peripheral blood.

EXAMPLES

The following examples are provided merely to further illustrate the invention. The scope of the invention is not construed to be limited to the examples.

Example 1

Cases in which Patients Survived Over a Long Period

Case 1

Figure 1:
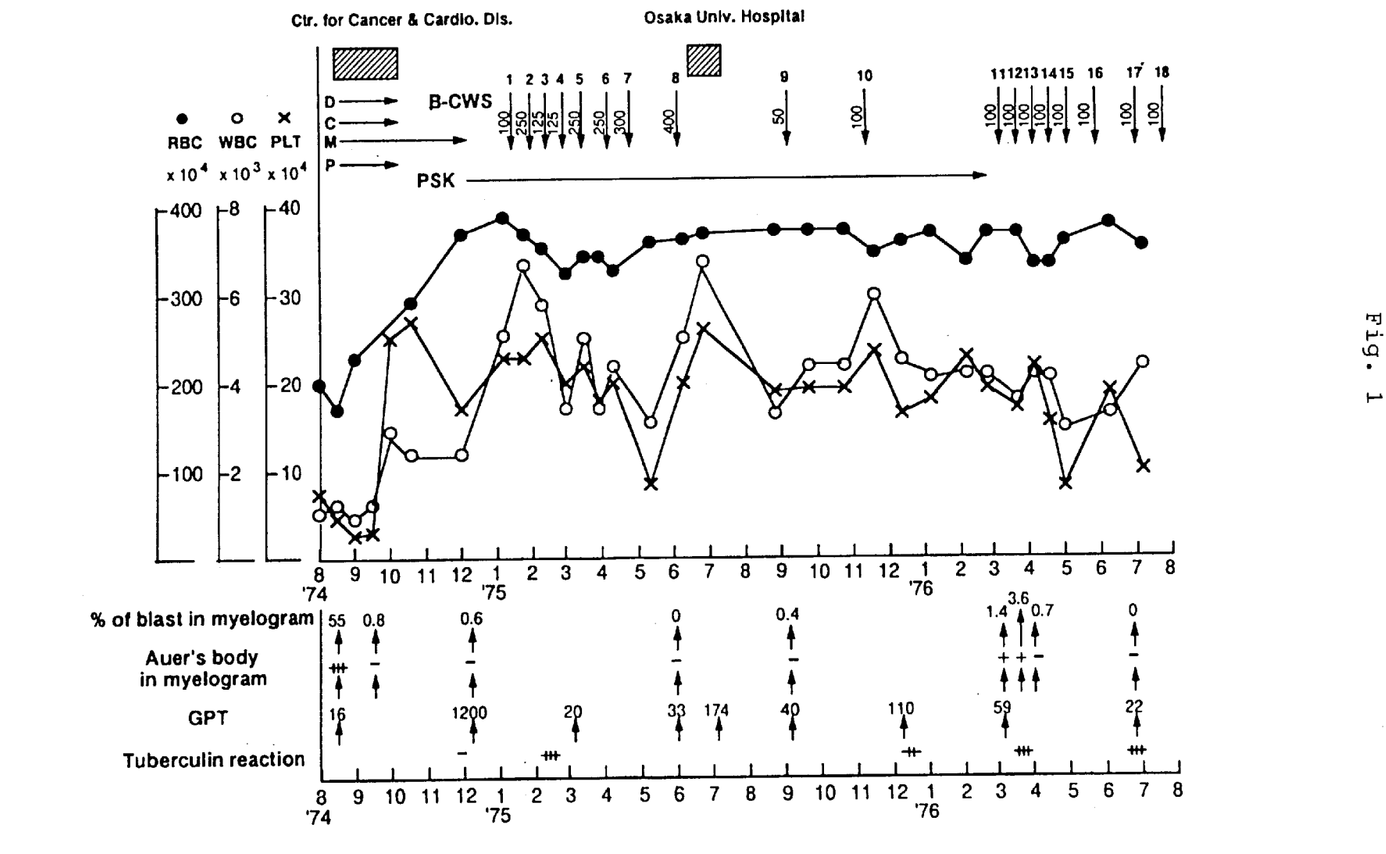
FIG. 1 shows clinical course of acute promyelocytic leukemia patient treated by immunotherapy with BCG-CWS alone.

Patient in Case 1 survived over a long period. The patient was suffering from typical acute promyelocytic leukemia. The patient who had been an outpatient of Osaka University Hospital was transferred to Osaka Medical Center for Cancer and Cardiovascular Diseases in order to start the independent immunotherapy after induction of complete remission. As shown in FIG. 1, the patient was pretty easily induced to remission by chemotherapy. However, since the patient had been participated in a clinical trial for PSK (Crestine), which may have caused an irregular immunotherapy with independent use of BCG-CWS and, recurrence of cancer occurred in about one and a half years after the beginning of the immunotherapy. Then, without repeated chemotherapy, the immunotherapy with independent use of BCG-CWS alone resumed. After about 3 weeks, Auer body in the patient's peripheral blood completely disappeared, and thereafter, the patient has been living a normal and healthy life for 22 years without recurrence (see FIG. 1).

This is the first case that a recurrent acute promyelocytic leukemia has completely cured by the immunotherapy with independent use of BCG-CWS alone.

Case 2

Case 2 is for a 72-year-old female patient suffering from a solid cancer (colon cancer) who survived over a long period of time. Her cancer was discovered upon crisis of ileus. She received continued chemotherapy after surgical operation, and then, clinical course was observed, which revealed that CEA (carcinoembryonic antigen) which once had favorably declined started to increase again, and at the same time, carcinomatous peritonitis had been accompanied. The immunotherapy with independent use of BCG-CWS alone was started, ascites disappeared, and CEA completely recovered to normal level, which was never elevated thereafter. She survived for 15 years and died at the age of 87.

Case 3

Patient in Case 3 was suffering from acute myelocytic leukemia, and has also survived long time. After the patient's successful remission induction, immunotherapy with independent use of BCG-CWS alone was started and thereafter, the patient has survived in good health for nearly 20 years without having recurrence.

Case 4

Case 4 is for a female patient suffering from lung cancer (large cell carcinoma). She had surgical operation, followed by post-operative immunotherapy with independent use of BCG-CWS alone, and has been surviving for 6 years in good health. She gave a chance for us to discover that the increase of IFN-γ level in patient's peripheral blood is an index for determination of therapeutic effect of immunotherapy.

Example 2

Time Dependent Changes of Biological Indices Accompanying BCG-CWS Inoculation

Peripheral blood was obtained from a patient who was inoculated with BCG-CWS, and blood levels of about 12 types of cytokines were determined by conventional ELISA. The results revealed that G-CSF, IL-6, and IFN-γ appeared in the peripheral blood.

Figure 2:
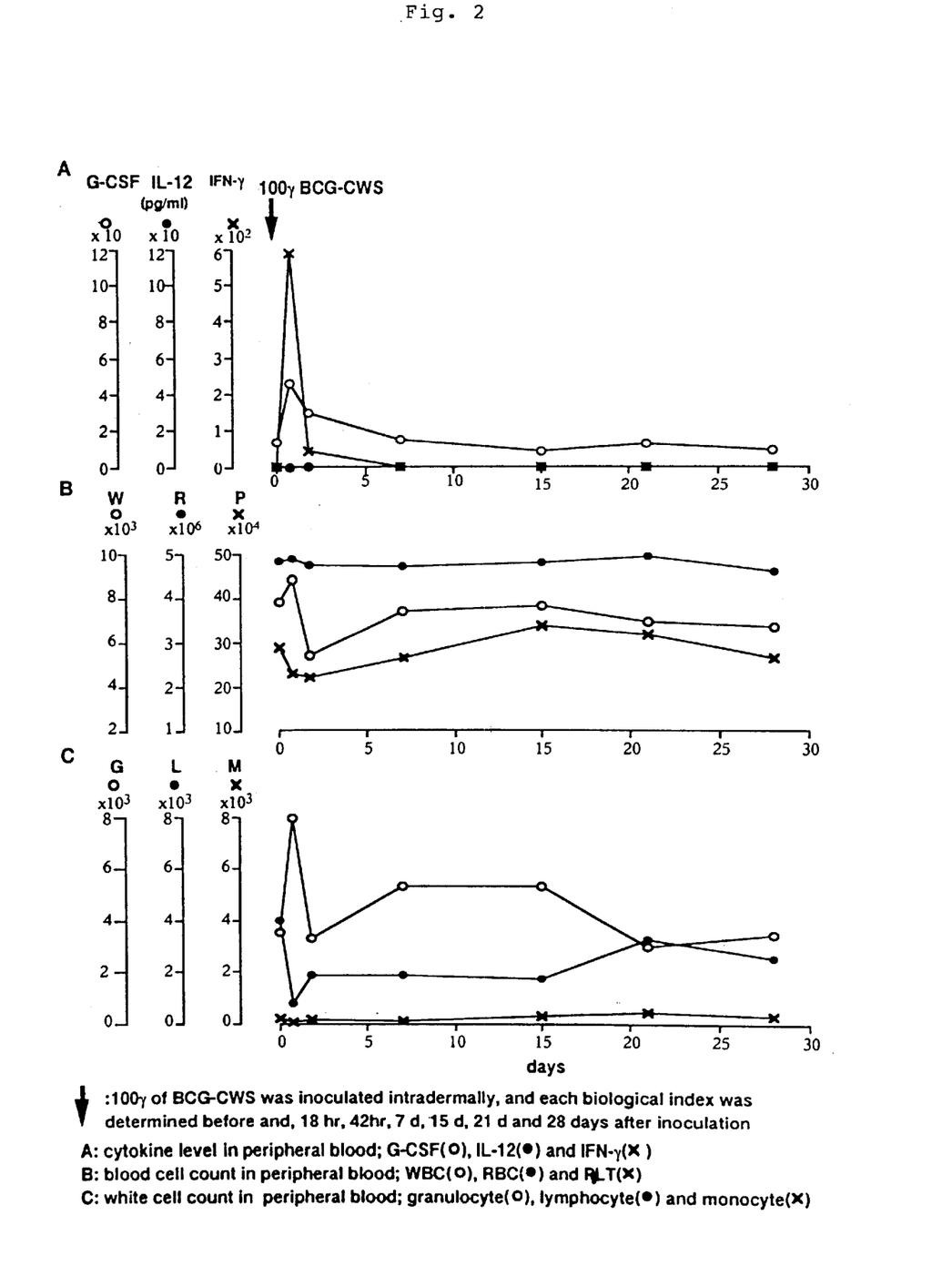
FIG. 2 shows time dependent changes of biological indices accompanying intradermal inoculation of $100\gamma$ of BCG-CWS. Determination of the indices was performed before, and 18 and 42 hours, and 7, 15, 21, and 28 days after inoculation.

FIG. 2 shows the time dependent changes of biological indices after inoculation of 100γ of BCG-CWS. FIG. 2A shows the level of cytokines (G-CSF, IL-12, IFN-γ) in peripheral blood, FIG. 2B shows the number of blood cells (white blood cell, red blood cell, platelet) in peripheral blood, and FIG. 2C shows white blood cell count (granulocyte, lymphocyte, monocyte), in peripheral blood.

After inoculation of BCG-CWS, the induction of G-CSF and INF-γ, particularly remarkable induction of IFN-γ occurred, having its peak around about 15 to 18 hours after inoculation. At the same time, leukocytosis, thrombocytopenia, especially granulocytosis, and lymphopenia occurred, although induction of IL-12 was not observed. Interestingly, IFN-γ in peripheral blood disappeared in about 30 hours (see FIG. 2).

Example 3

Figure 3:
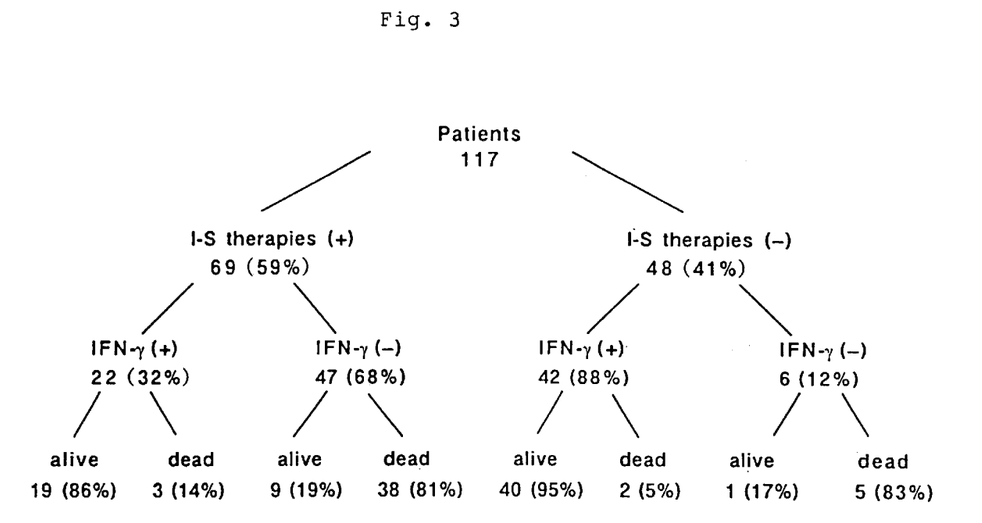
FIG. 3 shows the effects of immuno-suppressive (I-S) therapy on IFN-$\gamma$ induction test and prognosis of patients treated with BCG-CWS alone. "I-S therapies" in the figure means chemotherapy and/or radiation therapy before BCG-CWS immunotherapy. The results of IFN-$\gamma$ induction test were obtained at the time of the fourth inoculation in the sensitization phase (S4) and at the first inoculation in the therapeutic phase (T1). Alive or dead was evaluated at 6 months after the beginning of BCG-CWS immunotherapy.

Influence of Immuno-suppressive Therapy on IFN-γ Induction Test and Prognosis of Patients Treated with Independent use of BCG-CWS Alone Up to now, 117 patients have undergone IFN-γ induction test. The results obtained were analyzed by dividing the patients into two groups, i.e., a group of patients who received immuno-suppressive therapy comprising anti-cancer agent or radiation before starting immunotherapy with independent use of BCG-CWS alone, and a group of patients who did not receive such therapy. As shown in FIG. 3, the rate of IFN-γ positive patients was as low as about 30% in the immuno-suppressive therapy group, while it was as high as about 90% in the non-immuno-suppressive therapy group. In the IFN-γ positive patients, about 90% of the patients survived more than 6 months after the beginning of the therapy with BCG-CWS, irrespective of the presence or absence of the immuno-suppressive therapy. On the other hand, the number of survivors in the IFN-γ negative group is fewer than that in the IFN-γ positive ones, and only about 20% of the patients survived more than 6 months after the beginning of the therapy with BCG-CWS. The above results show that anti-cancer agents or radiation therapy greatly affects the immuno-competence of a patient, and therefore, BCG-CWS is preferably used alone not combined with anti-cancer agents or radiation therapy.

Example 4

Cancer Patients who Received Immunotherapy with Independent Use of BCG-CWS Alone Up to now, an agent for cancer immunotherapy with independent use according to the present invention has been applied to 181 cancer patients. Among them, the number of patients suffering from lung cancer was the largest (75 patients). However, the patients who received the therapy covered almost all sorts of cancers, including such as stomach cancer, colon cancer, and breast cancer.

Figure 4:
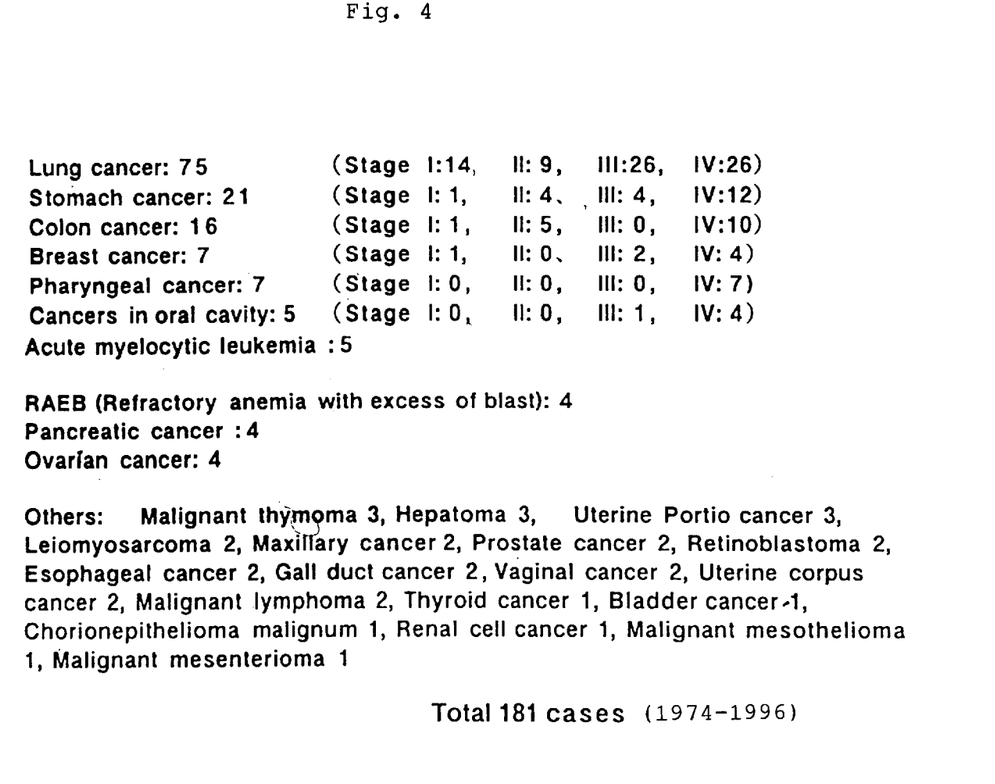
FIG. 4 shows the number of patients with various kinds of cancer treated with BCG-CWS immunotherapy alone.

According to classified stages, the number of patients in Stage IV is the largest (FIG. 4).

Example 5

Figure 5:
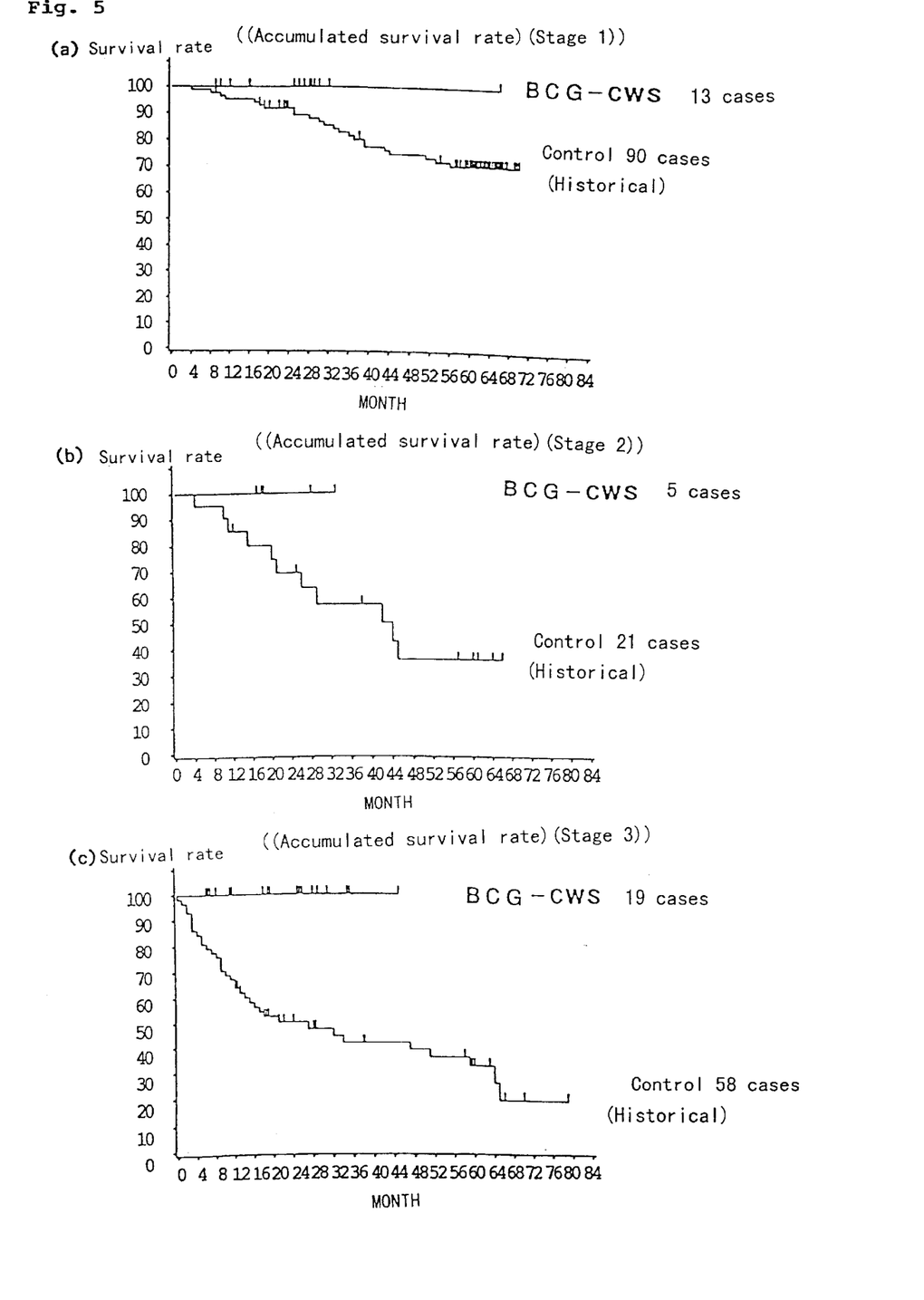
FIG. 5 shows the comparison of the survival curve of primary lung cancer patients who received post-operative immunotherapy with independent use of BCG-CWS alone, and the survival curve of historical control patients who received surgical operation at Osaka Medical Center for Cancer and Cardiovascular Diseases during 1988 to 1989. The statistical evaluation of test of significance by Log-Rank and Wilcoxon methods are p=0.2287 and p=0.2313 for Stage I, p=0.2037 and p=0.2115 for Stage II, p=0.0009 and p=0.0012 for Stage III, respectively.

Effect of Post-operative Independent Immunotherapy on Patients Suffering from Primary Lung Cancer In the patients suffering from primary lung cancer (non-small cell lung cancer), the number of which was the largest in the present study, a group of patients who underwent post-operative immunotherapy with independent use of BCG-CWS alone and historical control patients given surgical operation at Osaka Medical Center for Cancer and Cardiovascular Diseases during 1988 to 1989 were analyzed by Kaplan-Meyer method, and then, survival curves obtained for each group were compared (FIG. 5). As a result, all of the patients who received immunotherapy with independent use of BCG-CWS alone at Stages I, II, and III survived. In Stage III, remarkably significant difference that had not been reported was found between the two groups (p=0.0009 by Log-Rank method and p=0.0012 by Wilcoxon method).

Example 6

Figure 6:
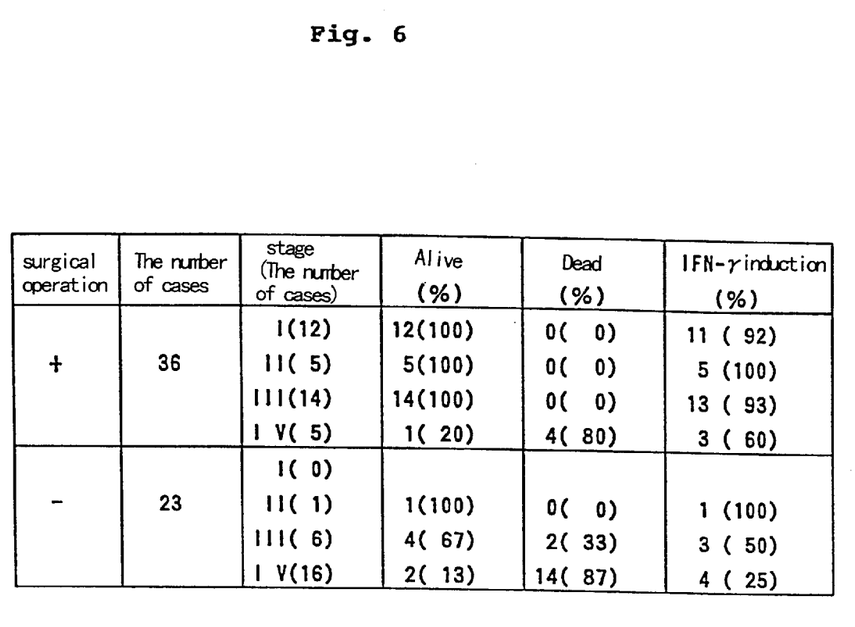
FIG. 6 shows the comparison of the effects of immunotherapy with independent use of BCG-CWS alone on primary lung cancer patients between those received surgical operation and those were inoperable.

Patients Suffering from Primary Lung Cancer who Received Immunotherapy with Independent Use of BCG-CWS Alone Therapeutic effect of immunotherapy with independent use of BCG-CWS alone on primary lung cancer patients who received surgical operation was compared with that on the patients to whom surgical operation was not applicable (FIG. 6). In the former, prognosis of patients who dared to undergo surgical operation at Stage IV was poor when compared to that at Stages I, II, and III, and about 80% of the patients died. Most of the patients in the latter were at Stages III and IV, particularly Stage IV, and prognosis of the patients was significantly poor. Most of the patients had undergone therapy using anti-cancer agent or radiation which decreased their immuno-competence, and therefore, they were not the subjects for the present immunotherapy.

These inoperable patients, if they showed positive IFN-γ induction, had all distant metastasis in the brain, liver, bone, or the like.

Example 7

A Case in which Metastasis in the Lymph Node was Cured

Figure 7:
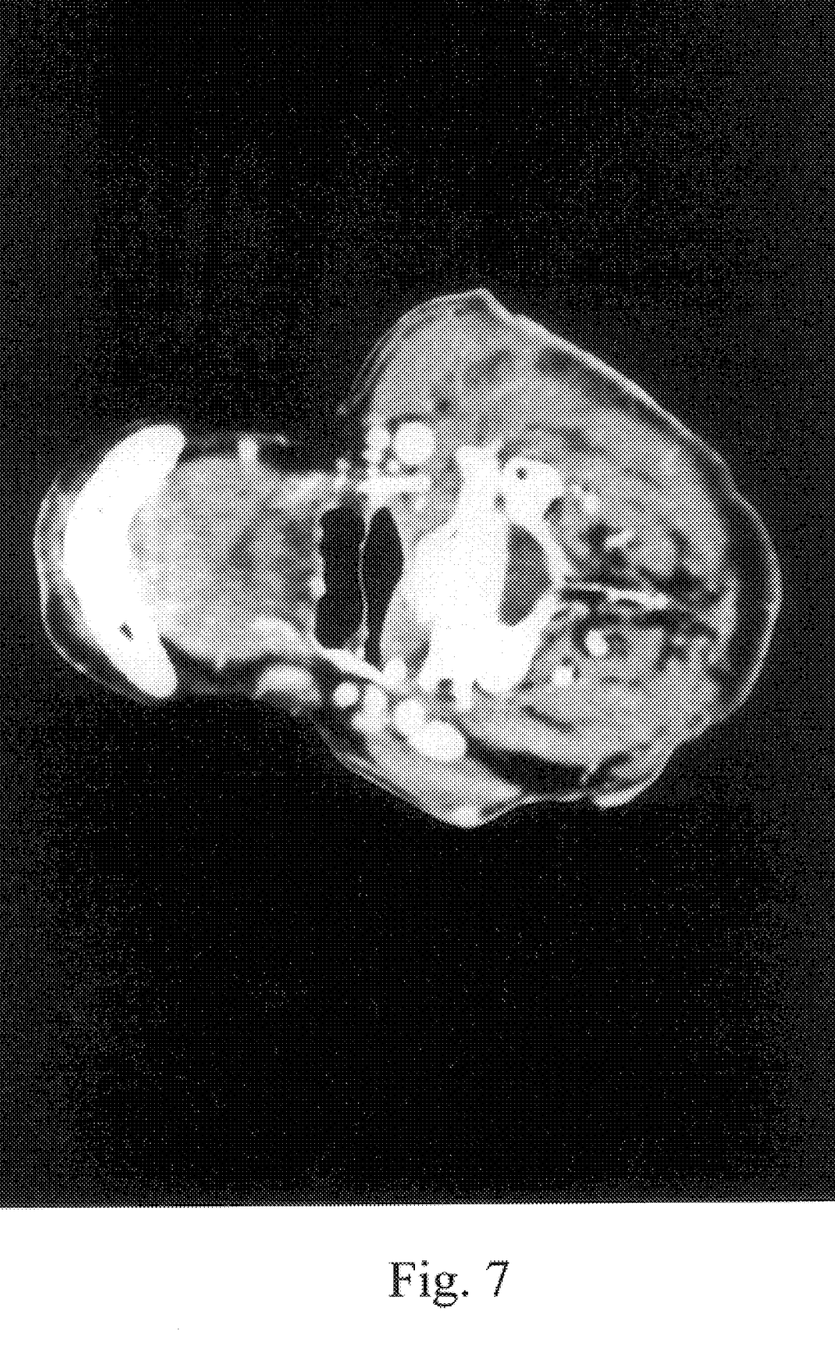
FIG. 7 is a copy of photograph of cervical CT scanning in a lung cancer patient (large cell carcinoma) with metastasis in the cervical lymph node. This photograph shows the state after radiation therapy and before BCG-CWS immunotherapy for cancer.

In a male patient suffering from lung cancer (large cell cancer), metastasis in the cervical lymph node was found. He underwent radiation therapy but significant effect was not observed (see FIG. 7 which is a copy of photograph of cervical CT scanning after radiation therapy and before BCG-CWS immunotherapy).

Figure 8:
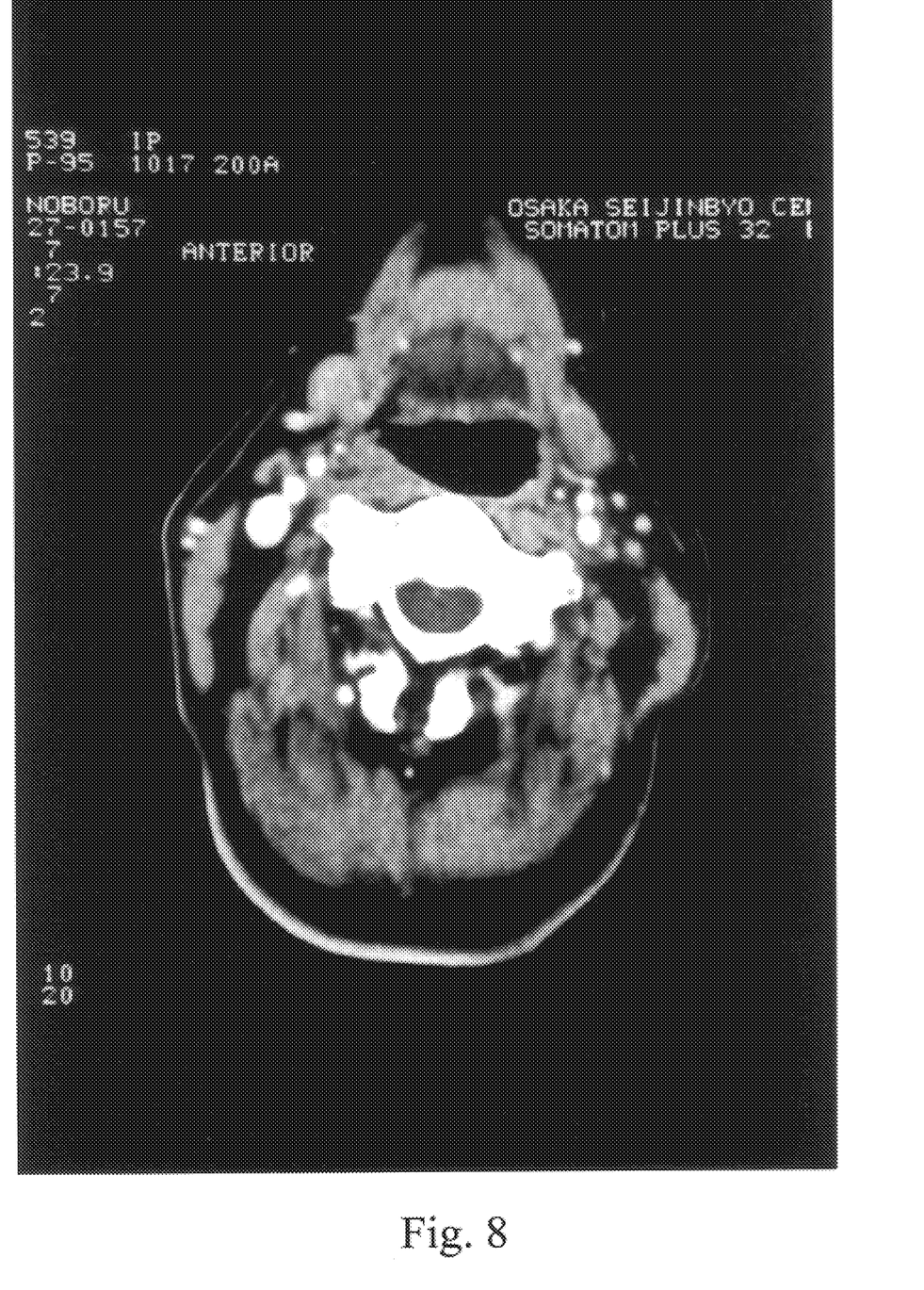
FIG. 8 is a copy of photograph of cervical CT scanning in a lung cancer patient (large cell carcinoma) with metastasis in the cervical lymph node. This photograph shows the state about one and a half years after the start of BCG-CWS immunotherapy.

Then, he underwent cancer immunotherapy with BCG-CWS alone, and swelling of the cervical lymph node almost disappeared 6 months after the beginning of the therapy, and swelling of the cervical lymph node was not observed after one and a half years (see FIG. 8 which is a copy of photograph of cervical CT scanning after the immunotherapy).

Example 8

Relationship between Changes in Constituents in Peripheral Blood after Inoculation of BCG-CWS and Effectiveness of Immunotherapy Upon inoculation of BCG-CWS, a series of changes in the constituents of peripheral blood were transiently observed. The changes closely related to the effectiveness of the immunotherapy as follows:

(1) Changes in the Components in Peripheral Blood from Patients to whom the Immunotherapy was Effective In 6 patients to whom the immunotherapy was successful and who are now alive in good health, increase in leukocytes, particularly granulocytes, and decrease in lymphocytes (continued about 24 hours) were found, having their peak at about 15 hours to about 18 hours after inoculation.

As for cytokines, increases in IFN-γ (continued about 30 hours) and G-CSF (continued about 1 week) were found.

Figure 9:
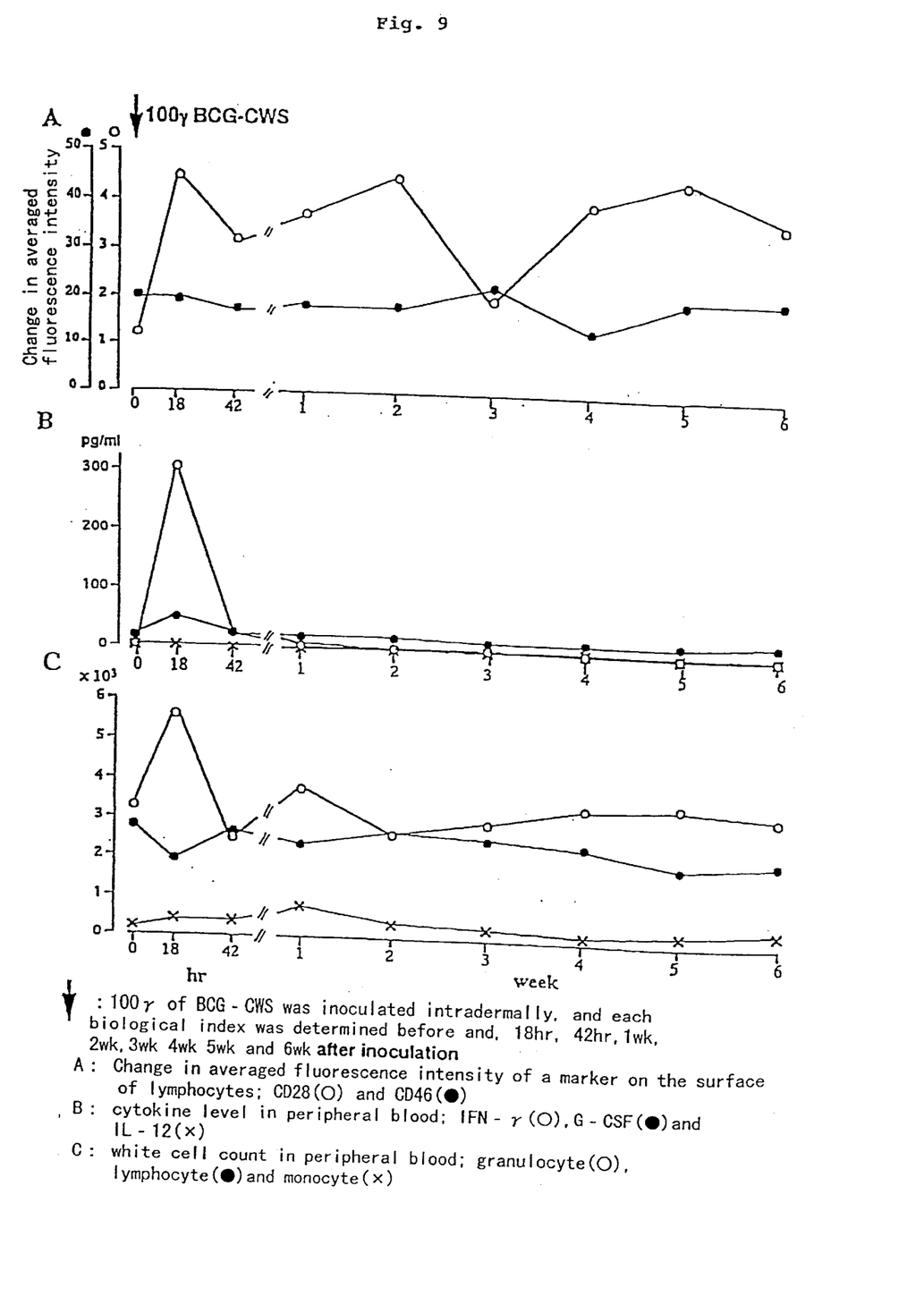
FIG. 9 shows the time dependent change of the components in peripheral blood, in particular, co-stimulatory signal CD28, from a patient after intradermal inoculation of $100\gamma$ of BCG-CWS. The patient was effectively treated by immunotherapy with BCG-CWS and survived in good health. Measurements of the components were performed before, and 18 and 48 hours and 1, 2, 3, 4, 5, and 6 weeks after BCG-CWS inoculation.

As for markers on the surface of T cell, increase in high CD28-positive lymphocyte group was found (continued about 4 to about 6 weeks). FIG. 9 shows the time dependent changes of the blood level of co-stimulatory signal, CD28 marker, expressed on T-lymphocytes derived from one of the patients to whom BCG-CWS immunotherapy was successful.

Materials and methods used for determination of markers on the surface of the T-cell, including CD28, are as follows:

1. Materials

Lymphocytes: To EDTA-added whole blood, Ficoll Plaque (Pharmacia) was added, and then, lymphocytes were isolated from the mixture, which were used within 2 hours after preparation.

Antibodies: Monoclonal antibodies to CD28 were obtained from Biochemical Engineering Co & Ltd., and monoclonal antibodies to CD46 were prepared in Osaka Medical Center for Cancer and Cardiovascular Diseases.

2. Flow Cytometry

Isolated lymphocytes were incubated with the above monoclonal antibodies, washed and fixed in a conventional manner, and then, analyzed by Epics Profile II (Coulter Co., Ltd.).

Figure 10:
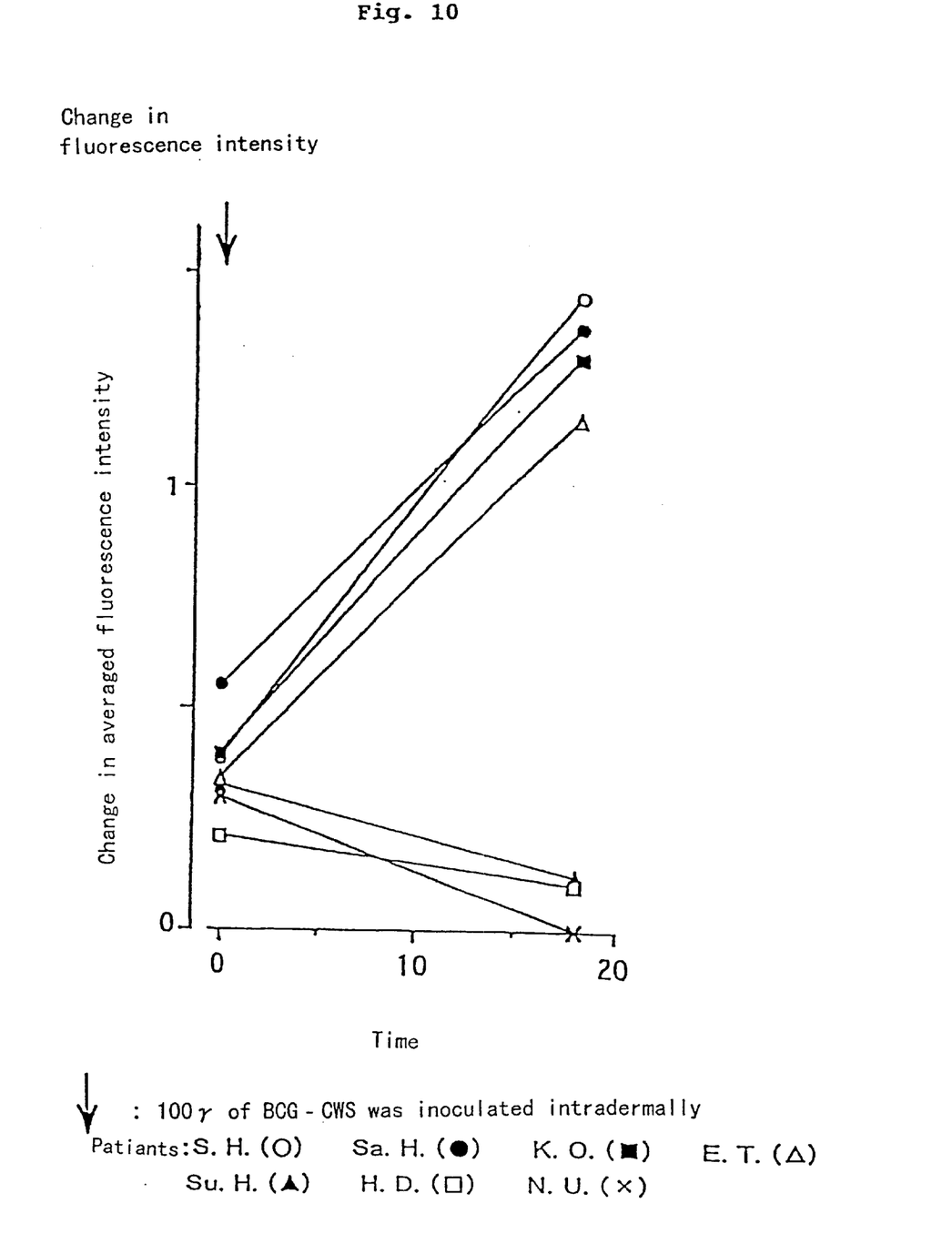
FIG. 10 shows changes in the level of co-stimulatory signal CD28 marker expressed on the lymphocytes from 7 patients who have been effectively treated by immunotherapy with BCG-CWS. In this trial, $100\gamma$ of BCG-CWS was inoculated intradermally. Measurement of marker was performed before and 18 hours after inoculation. Increase in the level of CD28 marker was observed in 4 among 7 patients (S.H., Sa.H., E.T., K.O.).

FIG. 10 shows the results of comparison of CD28 markers before and after inoculation of BCG-CWS in 4 (S.H., Sa.H., E.T., K.O.) out of 6 patients to whom the above immunotherapy was successful, and 3 other patients (Su.H., H.D., N.U.) to whom their therapies were also effective. As shown in FIG. 10, three patients (Su.H., H.D., N.U.) who did not show an increase in CD28 marker among the above items such as an increase of IFN-γ had each spent healthy life. However, metastasis in the brain was found in 2 of those patients around 2 years later, and they eventually died. Remaining one patient is now alive in good health 3 years after the therapy.

(2) Change in Components in Peripheral Blood from Patients to whom Immunotherapy was not Effective In one patient to whom immunotherapy was not effective, no changes was found in cellular components stated above, cytokines, especially IFN-γ, and markers on the surface of T-cell, especially CD28, and conditions of the disease of the patient are not good.

EFFECTS OF THE INVENTION

The present invention provides an immunotherapy for cancer which has advantageous merits stated below, that are not found in chemotherapy or radiation therapy.

(1) The immunotherapy provides a therapeutic effect of good quality. That is, complete cure can be expected with no recurrence of cancer and occurrence of secondary cancer over a long period of time.

(2) Low cost, above all.

(3) The therapy belongs to a non-specific active immunotherapy and it can deal with almost all sorts of cancer. It seems that the therapy produces killer cells specific to the cancer in respective patient.

(4) The therapy provides high quality of life (QOL) except for injury on the skin.

(5) Effects of the therapy can be fairly precisely predicted by the measurement of IFN-γ and CD28 marker, which allows the change of the therapy when therapeutic effects cannot be expected.

(6) A doctor can easily apply this therapy to patients, and one doctor can theoretically treat about 500 cancer patients simultaneously.

(7) There is no risk of tubercular infection or mixed infection in the injection spots, contrary to live BCG which has been put into practice for bladder cancer.

What is claimed is:

1. A method of testing immunocompetence in a cancer patient exposed to an immunotherapy with sole use of bacterial components, comprising:

determining the level of IFN-γ and CD28 marker in blood obtained from said patient who was administered said bacterial components intracutaneously, wherein an increase in the levels of IFN-γ and CD28 marker is indicative of immunocompetence.

2. The method according to claim 1, wherein said bacterial components suppress recurrence of the cancer or occurrence of secondary cancer.

3. The method according to claim 1, wherein said cancer patient is not suffering from lowering of immunocompetence, and does not have distant metastasis including that in the brain, liver, or bone.

4. The method according to claim 1, wherein said cancer patient has had remission induction or operation for removing primary lesion on initial therapy.

5. The method according to claim 4, wherein said patient has a solid cancer, and the initial therapy is a surgical operation.

6. The method according to claim 4, wherein said patient has a non-solid cancer, and the initial therapy is chemotherapy.

7. The method according to claim 1, wherein said patient has metastasis of cancer to the lymph node.

8. The method according to claim 1, wherein said patient has lung cancer.

9. A method of identifying a cancer patient who has immunocompetence suitable for the immunotherapy with sole use of bacterial components comprising:

determining the level of IFN-γ and CD28 marker in blood obtained from said cancer patient to whom said bacterial components were intracutaneously administered, wherein an increase in the levels of IFN-γ and CD28 marker is indicative of immunocompetence.

* * * * *